(12) United States Patent
Stark (10) Patent No.: US 7,399,973 B2
(45) Date of Patent: Jul. 15, 2008

(54) SYSTEM FOR MEDICAL DIAGNOSIS

(75) Inventor: Iain Stark, Manotick (CA)

(73) Assignee: Imaging PET Technologies, Inc. (CA)

( * ) Notice: Subject to any disclaimer, the term of this patent is extended or adjusted under 35 U.S.C. 154(b) by 143 days.

(21) Appl. No.: 11/084,173

(22) Filed: Mar. 18, 2005

(65) Prior Publication Data

US 2005/0269514 A1    Dec. 8, 2005

(30) Foreign Application Priority Data

Mar. 19, 2004   (CA) .................................. 2461964
Oct. 6, 2004    (CA) .................................. 2483953

(51) Int. Cl.
*G01T 1/161*   (2006.01)
*G01T 1/166*   (2006.01)
(52) U.S. Cl. .............................. 250/363.08; 250/363.05
(58) Field of Classification Search ............ 250/363.08, 250/363.05
See application file for complete search history.

(56) References Cited

U.S. PATENT DOCUMENTS

| | | | |
|---|---|---|---|
| 5,034,970 A | 7/1991 | Yahata et al. | |
| 5,057,692 A * | 10/1991 | Greskovich et al. | 250/361 R |
| 5,059,799 A | 10/1991 | Kurakake | |
| 5,554,848 A * | 9/1996 | Hermony et al. | 250/363.05 |
| 5,717,212 A | 2/1998 | Fulton et al. | |
| 5,966,422 A | 10/1999 | Dafni et al. | |
| 6,373,060 B1 * | 4/2002 | Yamakawa et al. | 250/363.08 |
| 6,617,582 B2 | 9/2003 | Stark | |
| 7,020,233 B1 * | 3/2006 | Tybinkowski et al. | 378/4 |
| 2005/0138731 A1 * | 6/2005 | Failor et al. | 5/601 |
| 2007/0069137 A1 | 3/2007 | Campbell et al. | |

FOREIGN PATENT DOCUMENTS

EP    1 005 257 A2    5/2000

* cited by examiner

*Primary Examiner*—David P. Porta
*Assistant Examiner*—Mindy Vu
(74) *Attorney, Agent, or Firm*—Berenato, White & Stavish, LLC (57) ABSTRACT

A system for medical diagnosis is provided. The system includes a gantry mounted on the base. The gantry has an annular support, which defines a cylindrical inner space. A detector head is fixed to the inner surface of the annular support. The annular support rotates along an axis of the inner space and is prevented from moving in horizontal and vertical direction and moving angularly. The system has a patient bed system, which is detachably attached to the base, and has a contact surface for supporting the patient. Pivot mechanism (s) and adjustable arm(s) enable the contact surface to have a plurality of configurations.

21 Claims, 9 Drawing Sheets

SYSTEM FOR MEDICAL DIAGNOSIS

FIELD OF INVENTION

The present invention relates to a system for medical diagnosis.

BACKGROUND OF THE INVENTION

Scintillation cameras are well known in the art of nuclear medicine, and are used for medical diagnostics. A patient ingests, inhales or is injected with a small quantity of a radioactive isotope. The radioactive isotope emits radiations that are detected by a scintillation medium in the scintillation camera. The scintillation medium is commonly a sodium iodide crystal, BGO or other. The scintillation medium emits a small flash or scintillation of light in response to stimulating radiation from a patient. The intensity of the scintillation light is proportional to the energy of the stimulating radiation, such as a gamma ray.

A conventional system for a scintillation camera such as a gamma camera includes a detector head, which detects gamma rays emitted from a patient and converts is them into electrical signals and a processor for processing the signals output from the detector. The detector head includes a scintillator and an array of photomultiplier tubes. The gamma rays are directed to the scintillator, which absorbs the radiation and produces a very small flash of light. The array of photodetectors, which are placed in optical communication with the scintillation crystal, convert these flashes into electrical signals which are subsequently processed. The processor processes the signals output from the array to produce an image of the distribution of the radioisotope within the patient.

For obtaining desired images, improvement has been achieved in this field. For example, a patient is placed on a flat bed, while a gamma camera(s) is rotated around a gantry and is further moved towards and away from the axis of rotation. Additional mechanical components may be added to angle the gamma camera, While such systems have improved the quality of the images, complicated arrangements are required to position the detector head. That affects the size of the system. Further, it is difficult to obtain supine and prone imagines in conventional systems that have limited rotation of 180° and operate on the principle of raising and lowering the detector on a vertical column. There is a need to mechanism by which a patient will not have to keep her/his posture standing during the operation, and thus feel comfortable.

It is, therefore, desirable to provide a new system with compact size and simple arrangement, which can easily and efficiently take desired medical images.

SUMMARY OF THE INVENTION

It is an object of the present invention to provide a new system, which obviates or mitigates at least one of the disadvantages described above.

The system uses a mechanism that enables the detector head to rotate within the inner space of the gantry and enables the system to obtain desired images without moving up/down or tilting the detector head. The system enables a patient to be supported in different ways.

In accordance with an aspect of the present invention, there is provided a system which includes: a base; a gantry mounted on the base, the gantry having an annular support ring, which defines a cylindrical inner space, and a detector head for taking image, which is fixed to the inner surface of the annular support ring; a mechanism for allowing the annular support ring to rotate along a centre axis of the inner space and for preventing horizontal, vertical and angular movements of the annular support; and a bed system for supporting and adjustably positioning a patient at a location with respect to the detector head.

In accordance with a further aspect of the present invention, there is provided a system for supporting and positioning a patient for medical diagnosis, including: (1) a contact surface for said patient including: (i) a back section having a first end and a second end; (ii) a seat section having a first end pivotably connected to the second end of the back section, and a second end; and (iii) a leg section having a first end pivotably connected to the second end of the seat section, and a second end, (2) a mechanism for enabling the contact surface to have a plurality of configurations, and including an arm pivotablly connected to one of the sections, and an actuator for actuating the arm; and (3) a controller for controlling the actuator to adjust a first angle between the back section and the seat section and a second angle between the seat section and the leg section through the arm.

A further understanding of other features, aspects and advantages of the present invention will be realized by reference to the following description, appended claims, and accompanying drawings.

BRIEF DESCRIPTION OF THE DRAWINGS

These and other features of the invention will become more apparent from the following description in which reference is made to the appended drawings wherein.

DETAILED DESCRIPTION OF THE PREFERRED EMBODIMENT(S)

Figure 1:
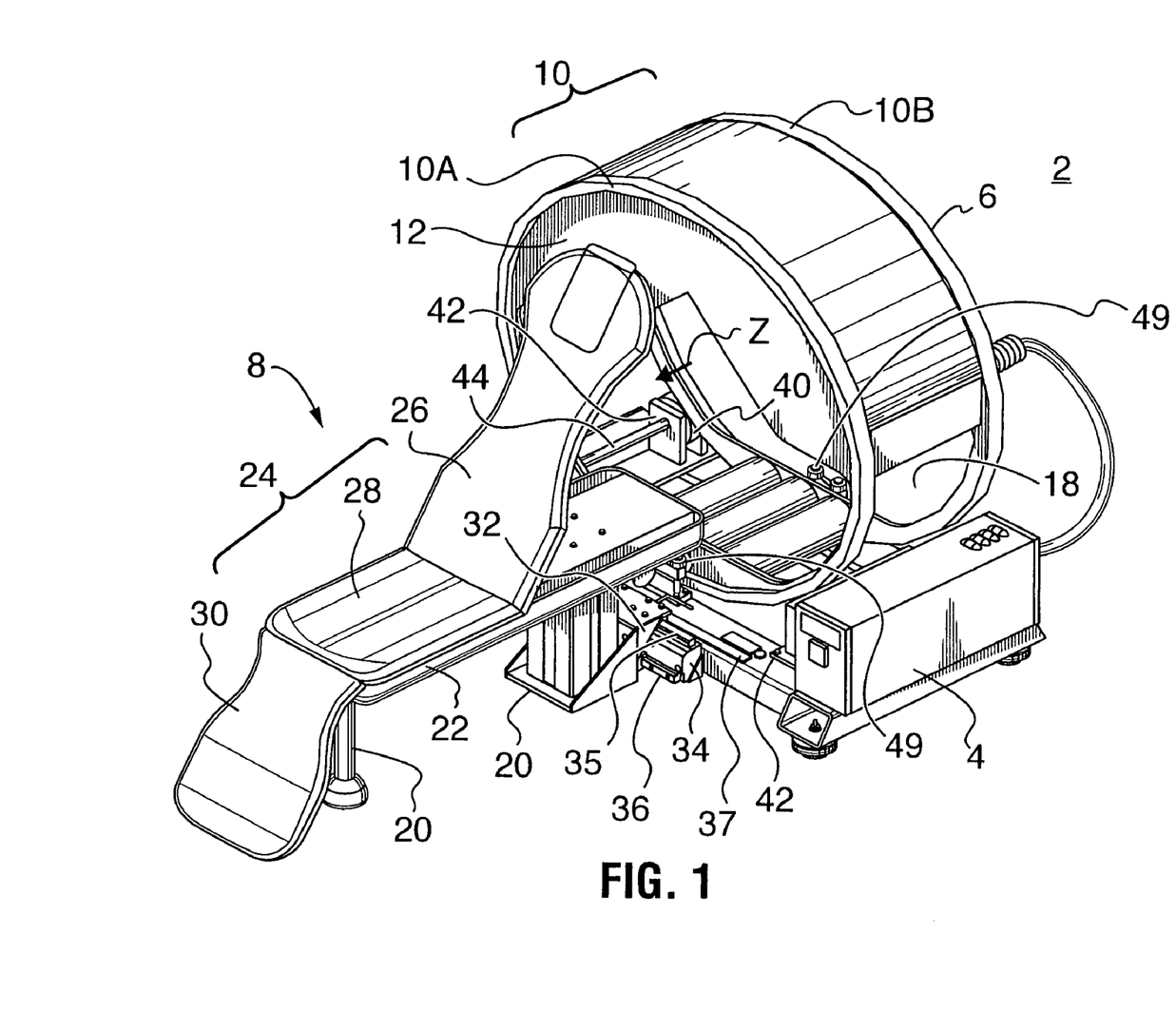
FIG. 1 is a perspective view showing a medical diagnosis system in accordance with an embodiment of the invention.

FIG. 1 shows a medical diagnosis system 2 in accordance with an embodiment of the present invention. The medical diagnosis system 2 includes a base 4, a gantry 6 for a medical nuclear camera and a patient bed system 8 for supporting and positioning a patient. The gantry 6 is mounted on the base 4, and has an annular support 10. The annular support 10 supports and guides a detector head 12 for the nuclear camera. The nuclear camera may be a scintillation camera or gamma camera, and may be a Cardiac Gamma Camera.

The base 4 has a fixing mechanism that enables the base 4 to be fixed on a flat plane (e.g. floor or wall) and a moving mechanism that enables the base 4 to move on the plane.

The annular support 10 has an inner surface (14 of FIG. 2) and an outer surface (16 of FIG. 2), and defines a cylindrical inner space 18. The detector head 12 is fused to the inner surface (14) of the annular support 10 so as to be positioned within the cylindrical inner space 18. A rotation mechanism for rotating the annular support 10 is provided. The rotation mechanism enables the annular support 10 to rotate along the center axis Z of the inner space 18, and prevents the annular support 10 from moving in a direction horizontal to the axis Z and in a direction vertical to the axis Z, and sliding and sloping about the axis Z. In FIG. 1, the annular support 10 includes a pair of annular rings 10A and 10B disposed parallel to each other.

The patient bed system 8 has a support base 20, a horizontal plane 22 on the base 20 and a patient support system 24. The patient support system 24 includes a contact surface (25 of FIG. 4) having a couch back support 26, a thigh support (or a seat) 28 and a leg support 30. The contact surface (25) for supporting the patient has a plurality of configurations as described below. Such configurations may be done by automatic control and/or manual control.

The patient bed system 8 is detachably attached to the base 4 through a connection element 32 located at the support base 20, which engages with a connection element 34 located at the base 4. The patient bed system 8 can move laterally with respect to the base on rails 35 and 36. An actuator 37 provides a controlled and reproduceable later motive power.

Figure 2:
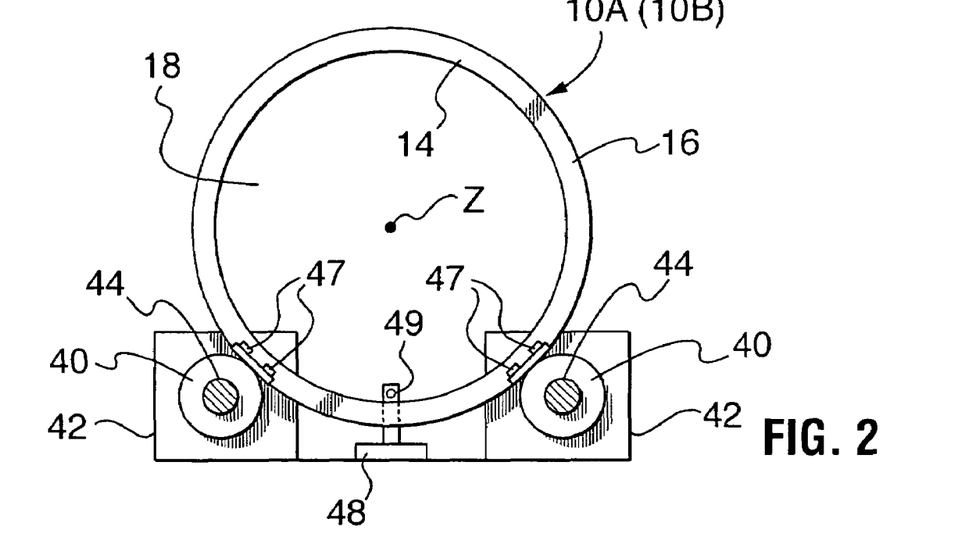
FIG. 2 is a diagram showing an example of the rotation mechanism provided to the annular support of FIG. 1.

The rotation mechanism of the annular support 10 is described in detail. FIG. 2 is an example of the rotation mechanism provided to the annular support 10. In FIG. 2, "14" represents the inner surface of the annular support 10 and "16" represents the outer surface of the annular support 10.

A roller 40 is provided to each side of the annular support ring 10A (10B). The roller 40 is rotatably mounted on a brace 42 fixed to the base 4. The roller 40 located at one side of the support ring 10A is connected to the roller located at the same side of the annular support ring 10B through a rod 44. The roller 40 engages with the outer surface 16 of the annular support 10 such that the annular support 10 is rotated by the roller 40. A drive unit (106 of FIG. 11) is provided to at least one roller 40 such that power is transferred from the drive unit to the roller 40. Cam followers 47 mounted on the brace 42 locate the annular support ring 10A in a support rings 10A not to be detached from the rollers 40, In FIG. 2, one ring 49 is shown. However, more than one ring 49 may be provided to each annular support ring as shown in FIG. 1.

Figure 3:
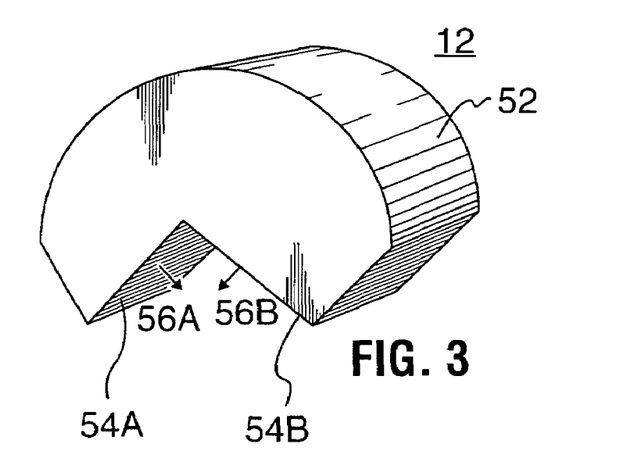
FIG. 3 is a diagram showing a housing of the detector head of FIG. 1.

The detector head 12 of FIG. 1 is now described in details. The detector head 12 has a V-shaped housing 52 as shown in FIGS. 1 and 3. The detector head 12 has two scintillation detectors disposed in the V-shaped housing 52. The housing 52 is rigidly fixed to the inner surface 14 of the annular support 10.

Referring to FIG. 3, the housing 52 has two planes 54A and 54B, which are connected to each other at substantially 90 degrees. Each detector has an array of photo multiplier tubes, a collimator plate and a scintillation crystal located on the corresponding plane. The collimator holes or channels extend to the surface of the surface of the corresponding collimator plate. The structure and components of the detector head 12 are, for example, disclosed on U.S. Pat. No. 6,617,582, which is incorporated herewith by reference.

The collimator plate for one detector is angled at substantially 90 degrees to the other detector, which prevents stay radiation from entering the collimator. This eliminates the requirement for lead shielding the detection field 56A and 5613 of the detectors. Thus, the detection fields 56A and 56B can be closer together, which minimizes risk of cutting off views during the operation.

Referring to FIGS. 4 to 10, one example of the patient support system 24 of FIG. 1 is described in details. The patient support system 24 adjusts a patient position and/or a patient posture as shown in FIGS. 4 to 10.

Figure 4:
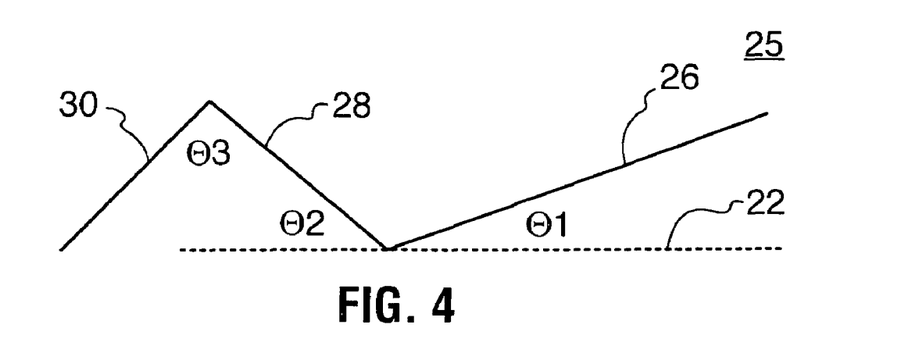
FIG. 4 is a schematic side view showing a contact surface of the patient is support system of FIG. 1.

FIG. 4 schematically illustrates the contact surface 25 having the couch back 23 support 26, the thigh support 28 and the leg support 30. "θ1" represents an angle between the couch back support 26 and the horizontal plane 22. "θ2" represents an angle between the thigh support 28 and the horizontal plane 22. "θ3" represents an angle between the thigh support 28 and the leg support 30. θ1, θ2 and θ3 are adjustable as described below.

Figure 5:
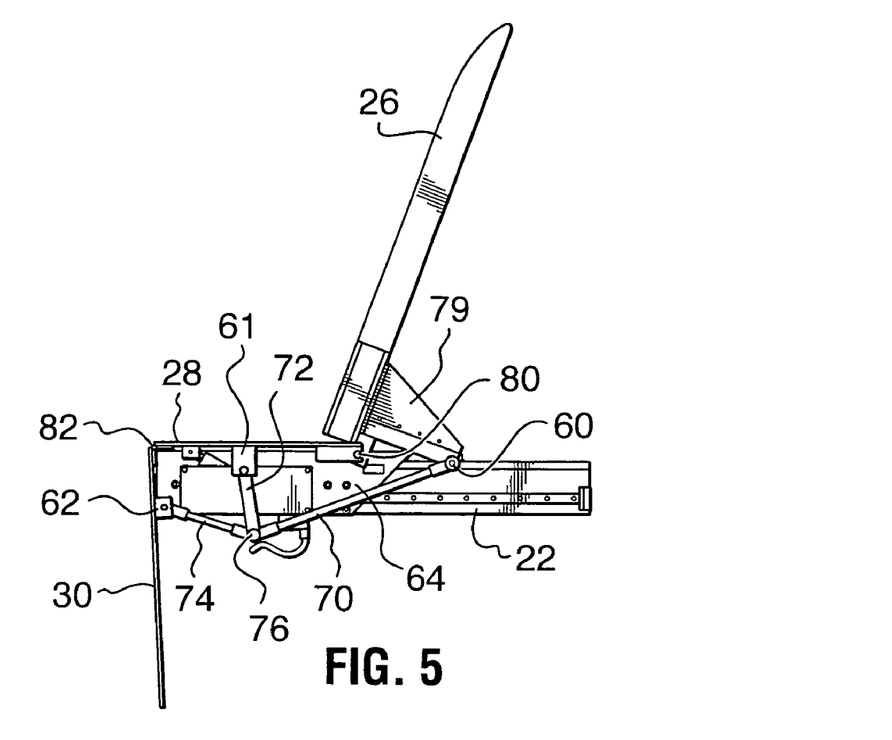
FIG. 5 is a side view showing one example of the patient support system and the configuration of the contact surface.
Figure 6:
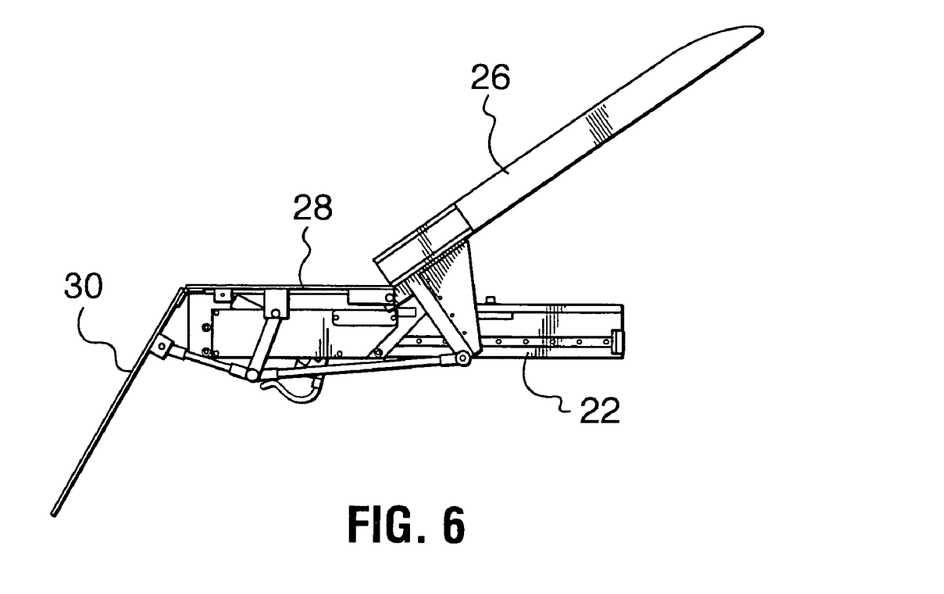
FIG. 6 is a side view showing further example of the configuration of the contact surface.
Figure 7:
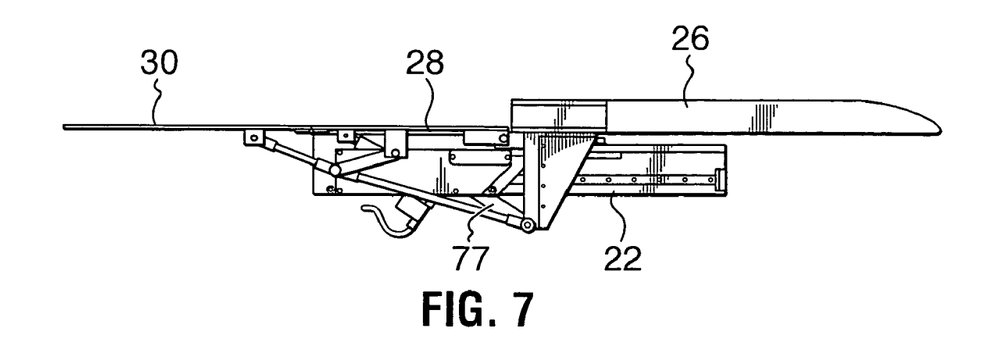
FIG. 7 is a side view showing further example of the configuration of the contact surface.
Figure 8:
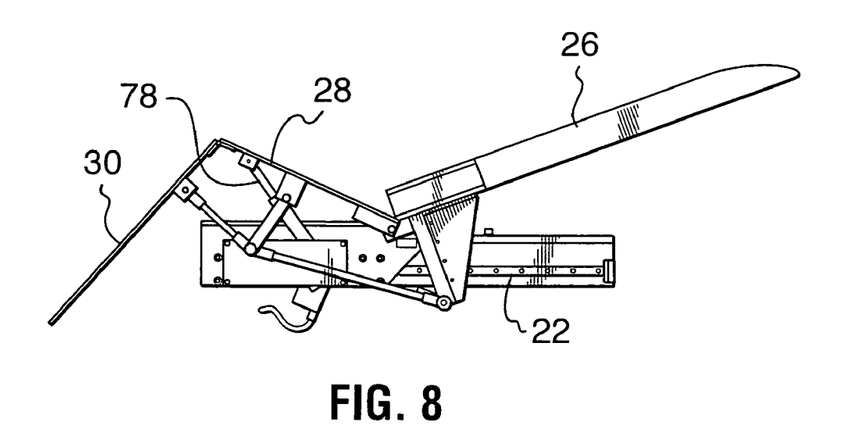
FIG. 8 is a side view showing further example of the configuration of the contact surface.
Figure 9:
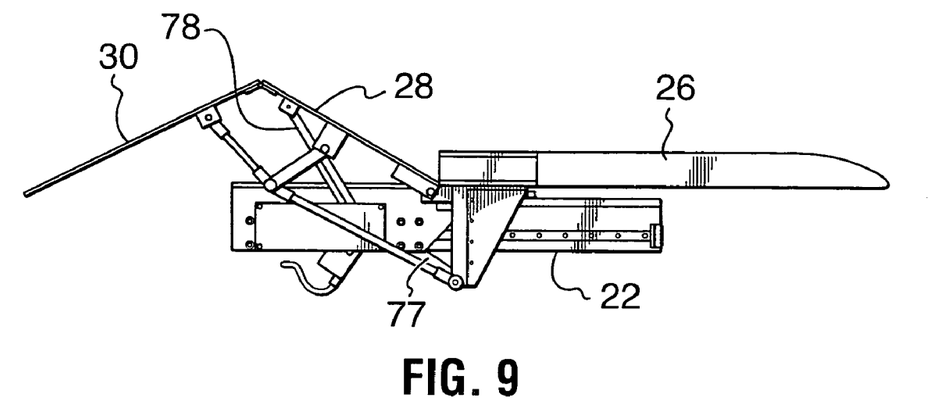
FIG. 9 is a side view showing further example of the configuration of the contact surface.
Figure 10:
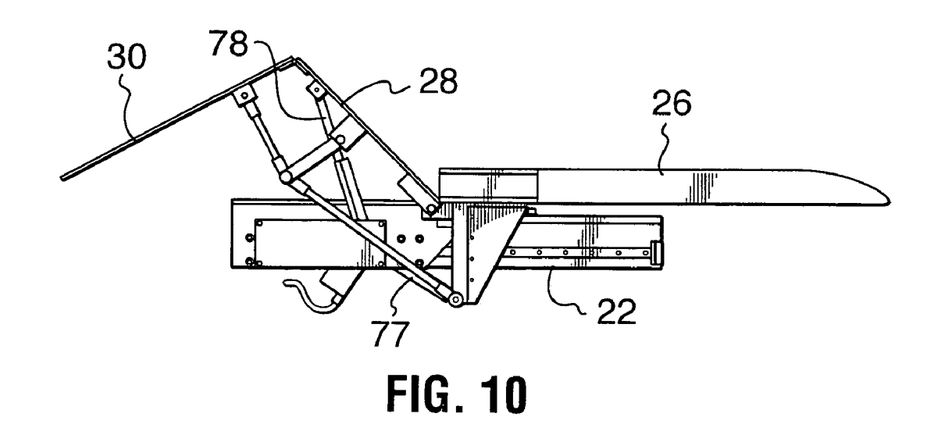
FIG. 10 is a side view showing further example of the configuration of the contact surface.

FIGS. 5 to 10 show examples of the configurations of the contact surface (25). In FIG. 5, the contact surface (25) is in a seat position, and forms a chair. In FIG. 6, the couch back support 26 and the leg support 30 are angled against the plane 22. In FIG. 7, the contact surface (25) is in a bed position and forms a flat bed. In FIGS. 8 to 10, the thigh support 28 is angled upwardly against the plane 22.

The couch back support 26, the thigh support 28 and the leg support 30 are linked together through a set of link arms 70, 72 and 74. One end of the link arm 70 is pivotably connected to a plate 79 through a pivot mechanism 60. The plate 79 is attached to the couch back support 26. One end of the link arm 72 is pivotably connected to the thigh support 28 through a pivot mechanism 61. One end of the link arm 74 is pivotably connected to the leg support 30 through a pivot mechanism 62. The link arms 70, 72 and 74 are pivotably connected to each other through a pivot mechanism 76. The pivot mechanism 76 may include a pivot point or axis. The pivot mechanism 76 enables the link arms 70, 72 and 74 to pivot around the pivot point or axis. The similar set of link arms may be provided to the other side of the supports 26, 28 and 30.

One end of the thigh support 28 and one end of the couch back support 26 are pivotably connected to each other through a pivot mechanism 80. The pivot mechanism 80 may include a pivot point or axis. The pivot mechanism 80 enables the supports 26 and 28 to pivot around the pivot point or axis.

The other end of the thigh support 28 and one end of the leg support 30 is pivotably connected to each other at a pivot mechanism 82. The pivot mechanism 82 may include a pivot point or axis. The pivot mechanism 82 enables the supports 28 and 30 to pivot around the pivot point or axis.

The seat 28 is on a sliding table 64. The sliding table 64 horizontally slides on the plane 22. Thus, the contact surface (25) is movable in a horizontal direction, One or more than one actuating arm are provided to the patient support system 24. An actuating arm (77 of FIG. 7) is connected to the axis of the pivot mechanism 60 or an edge of the plate 79. The length of the actuating arm 77 is adjustable. The actuating arm 77 changes its length under the control of an actuator (e.g., 37 of FIG. 1, 108, 110 of FIG. 11). An actuating arm (78 of FIG. 8) is connected to the thigh support 28. The length of the actuating arm 78 is adjustable. The actuating arm 78 changes its length under the control of an actuator (e.g., 37 of FIG. 1, 108, 110 of FIG. 11). For example, the back support 26 is angled downwardly when the actuating arm 77 shortens its length and pulls the back support 28 downwardly. For example, the thigh support 28 is angled upwardly when the actuating arm 78 extends its length and pushes the thigh support 28 upwardly.

The pivot mechanism 60, 61, 62, 76 or combinations thereof and the actuating arm 77, 78 or combinations thereof enable each support to pivot around its corresponding pivot axis or point (80, 82), and enable the contact surface (25) to have a number of configurations.

The configuration of the contact surface (25) can be converted in a plurality of different ways. For example, the patient for supine may be placed on the contact surface (25) as shown in FIG. 5. Then, the configuration of the contact surface (25) may be converted to that of FIG. 6. Further, the configuration of FIG. 6 may be converted to that of FIG. 7.

Referring to FIGS. 5 and 8 to 10, one example of the conversion for the contact surface (25) is described in detail. At first, the angles θ1 and θ2 are set to certain angles, such as 70° and 0°, respectively (FIG. 5). A patient is mounted on the patient support system 24. Then, the couch back support 26 is angled backwardly by a first actuator (e.g., 108 of FIG. 11). The angle θ1 is decreased at θ1=x° (<70°). "x°" may be adjusted by settings of relative actuator speeds.

When θ1 reaches the specific value x, a second actuator (e.g., 110 of FIG. 11) is powered. The thigh support 28 is angled upwardly by the second actuator. The angle θ2 is increased. The couch back support 26 is further angled backwardly such that the head of the patient moves downwardly. The leg support 30 is angled upwardly (FIG. 8). The knees of the patient are lifted.

Finally, the angle θ1 is 0, and the couch back support 26 is in its flat position (FIG. 9). The angle θ2 is set to a specific value, which is large enough so that the leg support 30 clears a trough. For example, θ2 is set to 32°, while the angle θ3 is 108°. The leg support 30 may be raised higher as required on a per patient basis (FIG. 10).

The data θ1, θ2 and θ3 may be pre-calculated for each patient based on his/her physical and/or medical information.

In the above description, θ1 is decreased; and θ2 and θ3 are increased. However, θ1, θ2 and θ3 can be increased and decreased in a number of different ways. A controller (e.g. 104 of FIG. 11) may have rules or algorithms to correlate θ1, θ2 and θ3 with each other.

Figure 11:
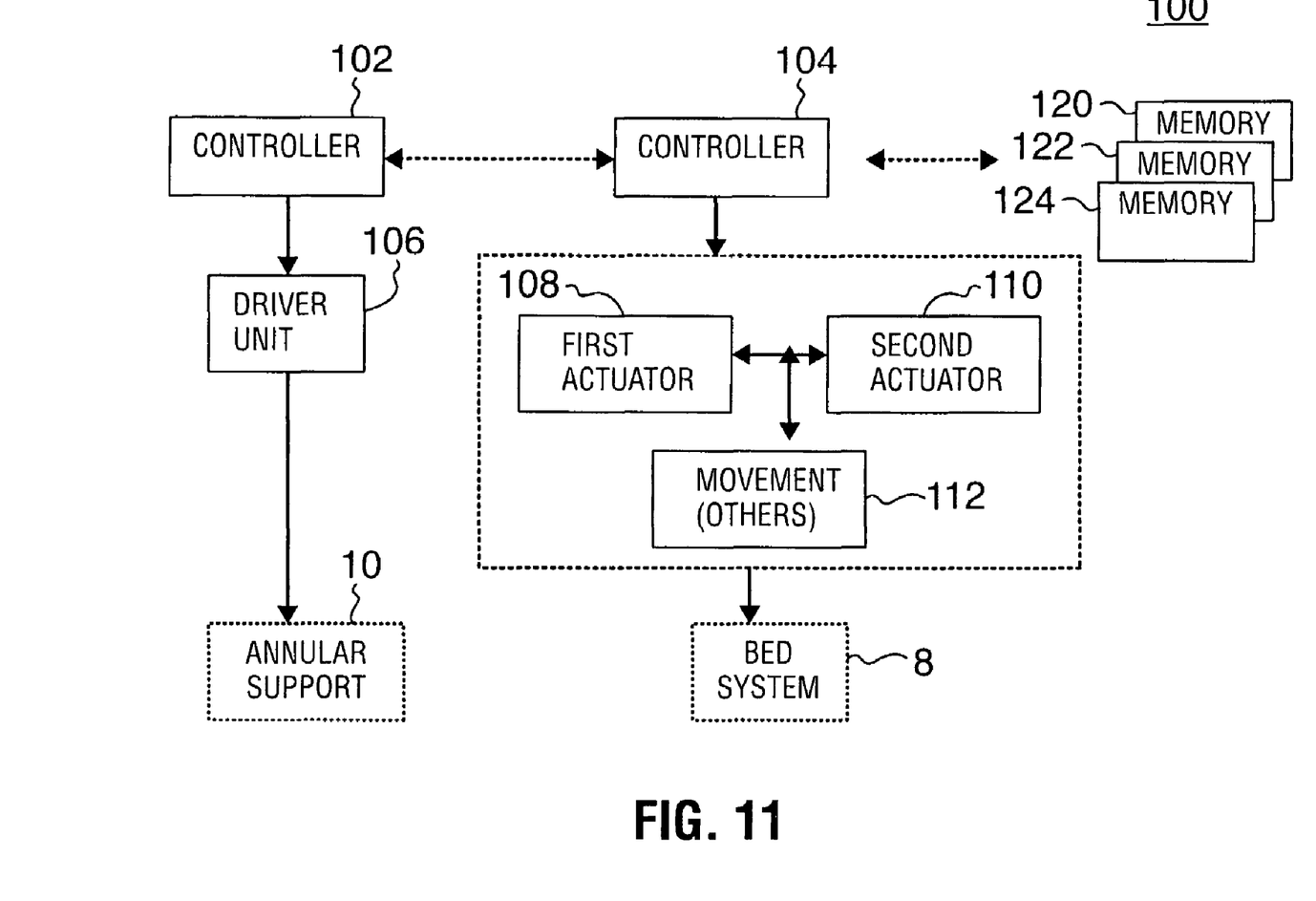
FIG. 11 is a block diagram showing a control system for the medical diagnosis system of FIG. 1.

FIG. 11 is a diagram showing a control system 100 for the medical diagnosing system 2 of FIG. 1. The control system 100 may be located on the base 4. The control system 100 includes a controller 102 for the annular support 10, and a controller 104 for the patient bed system 8. The controller 104 controls an actuator (e.g., 108, 110 or 108 and 110) for setting the patient support system 24 as described above. In FIG. 11, the actuators 108 and 110 are shown. However, only one actuator may be provided to the patient support system 24. The controller 104 may control the patient bed system 8 in cooperation with the controller 102.

Figure 12:
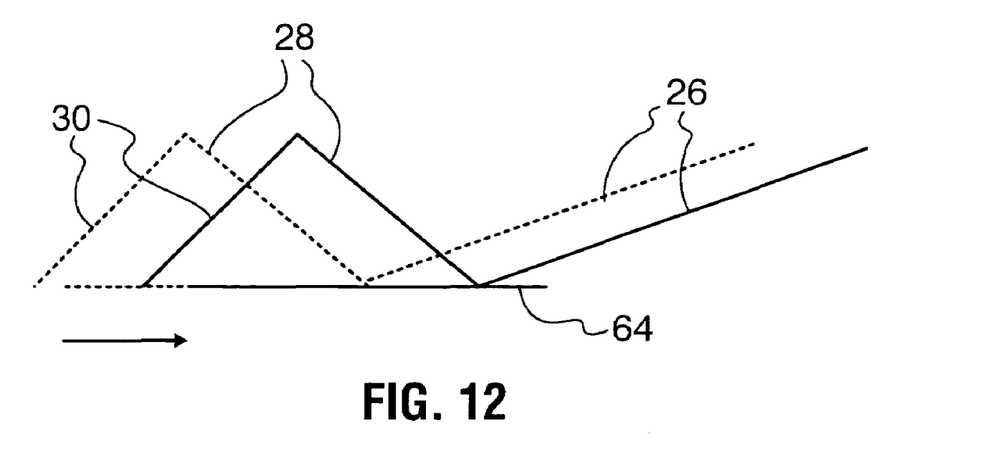
FIG. 12 is a schematic side view showing the horizontal movement of the contact surface.
Figure 13:
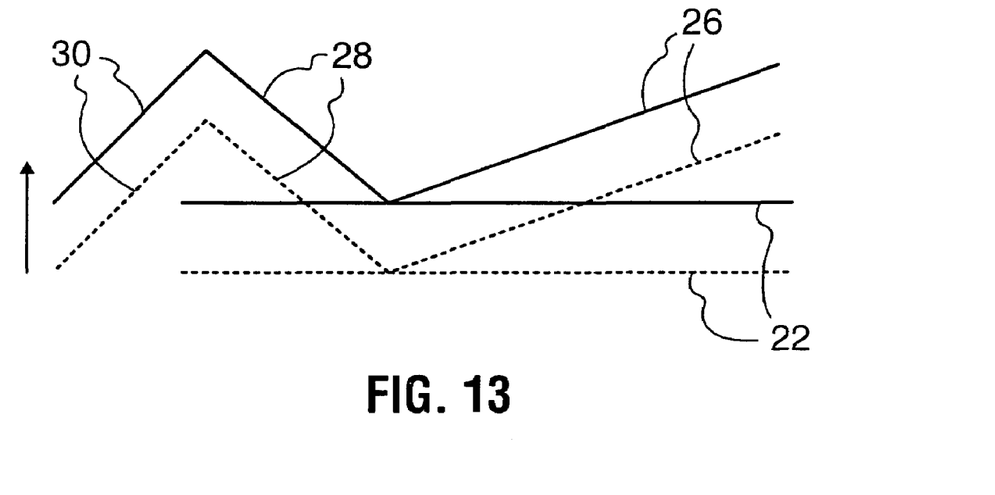
FIG. 13 is a schematic side view showing the vertical movement of the contact surface.

A movement mechanism 112 enables the position of a patient to be vertically and horizontally adjusted. The controller 104 controls the mechanism 112 for horizontally moving the sliding table (64 of FIG. 5) as shown in FIG. 12 and for vertically moving the horizontal plane 22 as shown in FIG. 13.

The control system 100 further includes an image memory 120 for storing projection images obtained by the detector head 12, a program memory 122 for image processing, and a memory 124 for storing information on a patient. The memory 124 stores, for example, patient's prone/supine information. When starting the operation of the medical diagnosis system 2, the patient may be suitable positioned based on the information pre-stored on the memory 124.

An output device (e.g. a display, a printer) and an input/control device (e.g. a keyboard, a mouse, a track ball) may be provided to the control system 100, and may be detachably connected to the base 4.

Figure 14:
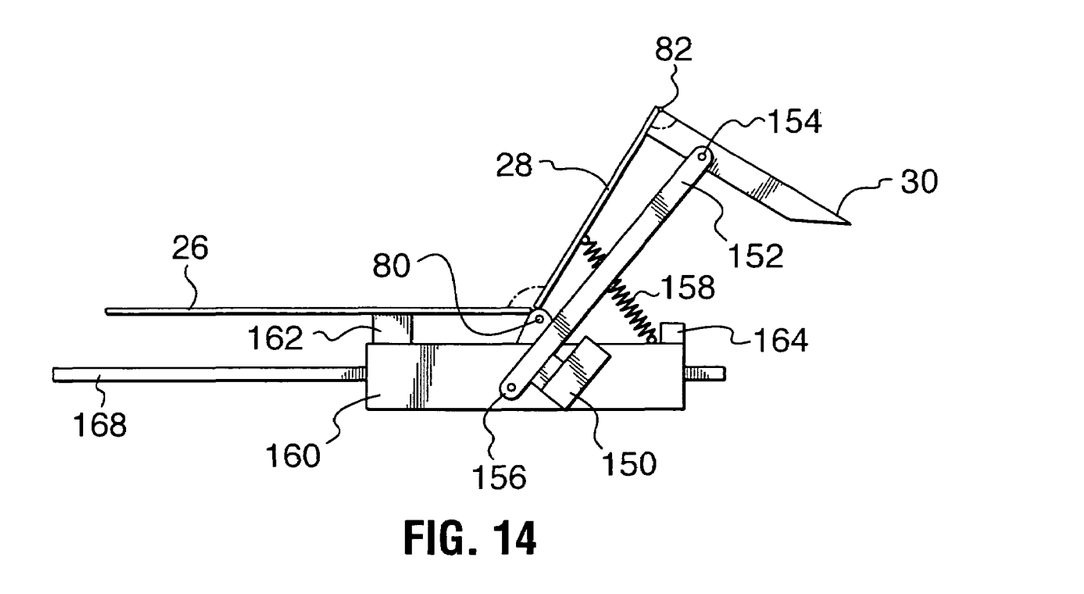
FIG. 14 is a side view showing another example of the patient support system and one configuration of a contact surface.
Figure 15:
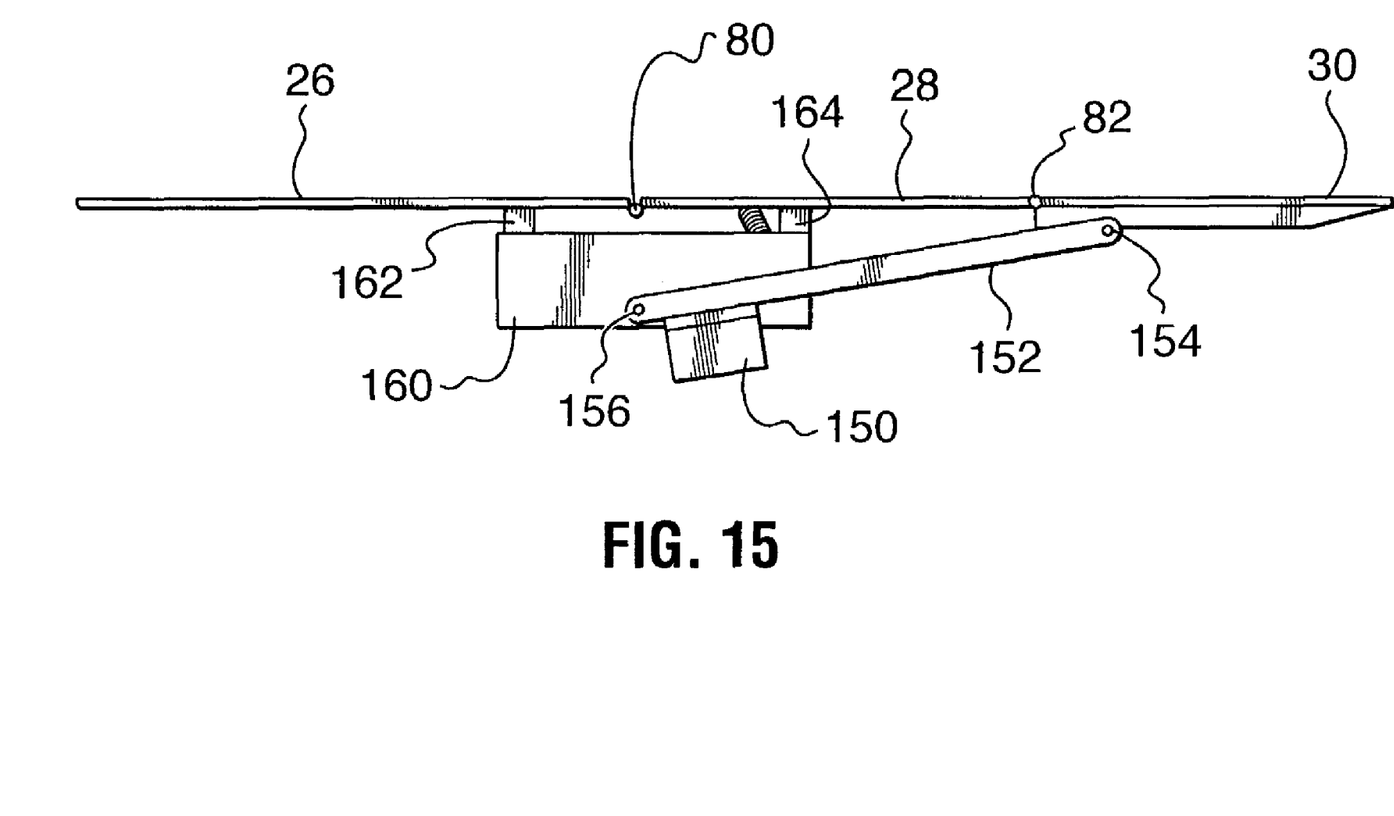
FIG. 15 is a side view showing another example of the configuration of the contact surface of FIG. 14.
Figure 16:
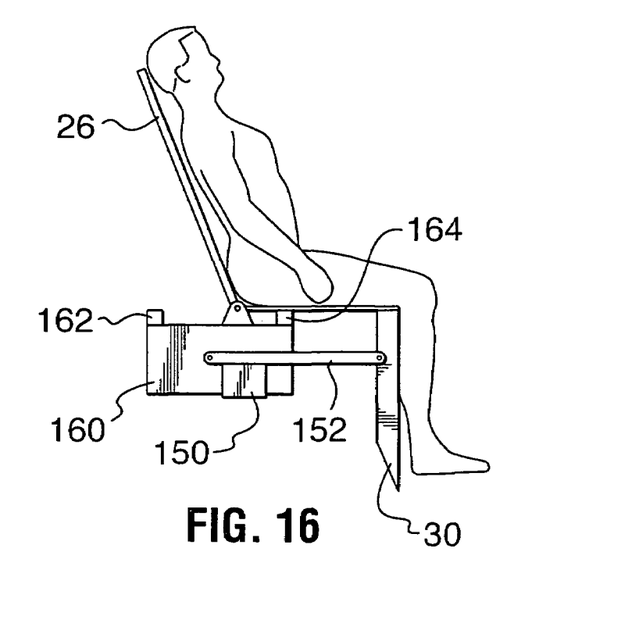
FIG. 16 is a side view showing father example of the configuration of the contact surface of FIG. 14.

FIGS. 14 to 16 show another example of the patient support system 24. In FIGS. 14 to 16, a single actuating arm is provided to the patient support system 24. The patient support system 24 of FIGS. 14 to 16 includes one actuator 150 for adjusting the contact surface (25) of the patient support system 24.

In FIGS. 14 and 15, the back support 26 is in a horizontal direction. In FIG. 16, the back support 26 is angled upwardly. In FIGS. 15 and 16, the seat 28 is in a horizontal direction. In FIG. 14, the seat 28 is angled upwardly.

The actuator 130 has a single actuating arm 152. One end of the arm 152 is pivotably connected to the leg support 30 through a pivot mechanism 154. The pivot mechanism 154 may has a pivot point or axis. The pivot mechanism 154 is configured to enable the leg support 30 and the arm 152 to pivot around the pivot point or axis.

A pivot mechanism 156 is provided to the other end of the arm 152. The pivot mechanism 156 may has a pivot point or axis. The pivot mechanism 156 is configured to enable the arm 152 to pivot around the pivot point or axis.

The back support 26 and the seat 28 are pivotably connected to each other through the pivot mechanism 80. The pivot mechanism 80 is configured to enable the seat 28 and the back support 26 to pivot around the pivot point or axis. The pivot mechanism 80 includes a base connected to a saddle 160.

The seat 28 and the leg support 30 are pivotably connected to each other through the pivot mechanism 82. The pivot mechanism 82 is configured to enable the seat 28 and the leg support 30 to pivot around the pivot point or axis.

The length of the actuating arm 152 is adjustable. The actuating arm 152 changes its length by the actuator 150.

The pivot mechanisms 154 and 156 and the actuating arm 152 enable the seat 28 and the leg support 30 to pivot around the pivot points or axes of the pivot mechanisms 80 and 82. The angle between the back support 26 and the seat 28, and the angle between the seat 28 and the leg support 30 are adjustable, and each is locked at a plurality of angles.

The pivot mechanism 156 may be slideable to adjust the position of the arm 152 against the saddle 160 and adjust the position of the leg support 30.

The back support 26 may be manually pivoted around the pivot mechanism 80, or automatically pivoted around the pivot mechanism by a controller (e.g. 104 of FIG. 11). The back support 26 can be locked at any angles. An adjustable actuating arm similar to the arm 77, 78 may be provided to the back support 26.

A stop element 162 is provided to the saddle 160 to support the back support 26 in a horizontal direction. A stop element 164 is provided to the saddle 160 to support the seat 28 in a horizontal direction. A spring mechanism (spring assist) 158 is provided between the seat 28 and the saddle 160. The saddle 160 is movable on rail(s) 168 in a horizontal direction.

When the actuator 150 pulls, the seat 28 and the back support 26 are locked at a certain angle as shown in FIG. 14. The seat 28 will lift the patient into an upright position. When the actuator 150 pushes, the patient is laid down for imaging. When the locks are released, the seat 28 and the leg support 30 straighten out as shown in FIG. 15. The angle between the seat 28 and the leg support 30 cannot exceed 180°. Also, the angle between the back support 26 and the seat 28 cannot exceed 180°. The stoppers 162 and 164 assure a flat bed position.

According to the embodiment of the present invention, the detector head 12 is located inside the gantry 6. Thus, the floor space for placing the system is reduced. As the movement of the detector head 12 is limited, complicated structural arrangements are not required comparing to the conventional systems. Further, the patient bed system 8 is detachably attached to the base 4. Thus, the gantry 6 with the detector head 12 and the patient bed system 8 can be moved separately from each other.

Since a patient can be placed at a desired position with respect to the detector head 12, it allows full range of nuclear medicine studies, and allows the system to obtain supine and prone images. Furthermore, the position of the patient is adjustable to comfort the patient.

The present invention has been described with regard to one or more embodiments. However, it will be apparent to persons skilled in the art that a number of variations and modifications can be made without departing from the scope of the invention as defined in the claims.

What is claimed is:

1. A system for medical diagnosis comprising:
a base;
a gantry mounted on the base, the gantry including an annular support defining a cylindrical inner space having a center axis and defining an outer surface of the gantry, the annular support having an inner surface;
a detector head for taking image, the detector head having a detector and a housing for the detector, the housing being fixed to the inner surface of the annular support so that the detector is placed in a fixed position from the annular support;
a mechanism rotating the annular support along the center axis and preventing horizontal, vertical and angular movements of the annular support; and
a bed system for supporting and adjustably positioning a patient at a location with respect to the detector head.

2. The system as claimed in claim 1, wherein the mechanism includes a drive unit for generating rotation movement, and a transfer element for transferring the rotation movement to the annular support.

3. The system as claimed in claim 2, wherein the housing is a V-shaped housing fixed to the inner surface of the annular support and a pair of detectors disposed in the V-shaped housing.

4. The system as claimed in claim 3, wherein the pair of the detectors are disposed at substantially 90 degrees to each other.

5. The system as claimed in claim 1, wherein the bed system is detachably attached to the base.

6. The system as claimed in claim 1, wherein the bed system includes a patient support for supporting the patient and a controller for controlling the configuration of the patient support.

7. The system as claimed in claim 6, wherein the patient support is capable of being in a chair position and in a flat bed position.

8. The system as claimed in claim 6, further comprising a mechanism for moving the bed system in vertical and horizontal directions.

9. The system as claimed in claim 1, wherein the bed system includes:
(1) a contact surface for said patient including:
   (i) a back section having a first end and a second end;
   (ii) a seat section having a first end pivotably connected to the second end of the back section, and a second end; and
   (iii) a leg section having a first end pivotably connected to the second end of the seat section, and a second end,
(2) a configuration mechanism having at least one arm pivotably connected to one of the sections and an actuator for actuating the arm; and
(3) a controller for controlling the actuator to adjust a first angle between the back section and the seat section and a second angle between the seat section and the leg section through the arm.

10. The system as claimed in claim 9, wherein one end of the arm is pivotably connected to the leg section or the back section.

11. The system as claimed in claim 10, further comprising a pivot mechanism to provide pivot movement to the other end of the arm.

12. The system as claimed in claim 11, wherein the position of the pivot mechanism is adjustable.

13. The system as claimed in claim 10, further comprising a mechanism for adjusting the position of the section which is unconnected to the arm.

14. The system as claimed in claim 9, wherein the first angle and the second angle can be locked.

15. The system as claimed in claim 9, further comprising a stopper for supporting the back section and the leg section in a horizontal direction.

16. The system as claimed in claim 9, wherein the actuator adjusts the length of the arm so as to push or pull the section pivotably connected to the arm.

17. The system as claimed in claim 1, wherein the annular support includes a pair of annular support rings, the pair of annular support rings disposed parallel to each other.

18. The system as claimed in claim 1, wherein the bed system comprises:
a contact surface having a plurality of sections for supporting the patient;
at least one arm pivotably connected to the contact surface; and
an actuator for actuating the arm to change the position of at least one of the sections.

19. The system as claimed in claim 18, wherein the bed system comprises:
a controller for controlling the actuator to adjust an angle between two adjacent sections among the plurality of sections.

20. The system as claimed in claim 18, wherein the bed system comprises:
a controller for controlling the actuator to adjust the length of the arm so as to push or pull the section pivotably connected to the arm.

21. A system for medical diagnosis comprising:
a base;
a gantry mounted on the base, the gantry including an annular support defining a cylindrical inner space having a center axis, the annular support having an inner surface;
a detector head for taking image, the detector head being fixed to the inner surface of the annular support;

a mechanism rotating the annular support along the center axis and preventing horizontal, vertical and angular movements of the annular support; and a bed system for supporting and adjustably positioning a patient at a location with respect to the detector head, the bed system comprising:

(1) a contact surface for said patient including:
   (i) a back section having a first end and a second end;
   (ii) a seat section having a first end pivotably connected to the second end of the back section, and a second end; and
   (iii) a leg section having a first end pivotably connected to the second end of the seat section, and a second end, (2) a configuration mechanism having at least one arm pivotably connected to one of the sections and an actuator for actuating the arm;

(3) a controller for controlling the actuator to adjust a first angle between the back section and the seat section and a second angle between the seat section and the leg section through the arm, wherein the actuator adjusts the length of the arm so as to push or pull the section pivotably connected to the arm.

* * * * *